US010639250B2

(12) United States Patent
Pöyry et al.

(10) Patent No.: US 10,639,250 B2
(45) Date of Patent: May 5, 2020

(54) METHOD OF PRODUCING A DISINFECTION FOAMABLE COMPOSITION

(71) Applicant: Nolla Antimicrobial Ltd, Valletta VLT (MT)

(72) Inventors: Juha-Pekka Pöyry, Ylöjärvi (FI); Jyri Nieminen, Ylöjärvi (FI)

(73) Assignee: Nolla Antimicrobial Ltd, Valletta, MT (US)

( * ) Notice: Subject to any disclaimer, the term of this patent is extended or adjusted under 35 U.S.C. 154(b) by 0 days.

(21) Appl. No.: 16/194,454

(22) Filed: Nov. 19, 2018

(65) Prior Publication Data

US 2019/0083373 A1    Mar. 21, 2019

Related U.S. Application Data

(62) Division of application No. 14/894,375, filed as application No. PCT/FI2014/050430 on May 28, 2014, now abandoned.

(30) Foreign Application Priority Data

May 28, 2013 (FI) ..................... 20135578

(51) Int. Cl.
| | | |
|---|---|---|
| *A61K 8/19* | (2006.01) | |
| *A61K 8/40* | (2006.01) | |
| *A61Q 17/00* | (2006.01) | |
| *A61K 8/84* | (2006.01) | |
| *A61K 8/04* | (2006.01) | |
| *A01N 55/02* | (2006.01) | |

(52) U.S. Cl.
CPC ............... *A61K 8/19* (2013.01); *A01N 55/02* (2013.01); *A61K 8/046* (2013.01); *A61K 8/40* (2013.01); *A61K 8/84* (2013.01); *A61Q 17/005* (2013.01); *A61K 2800/30* (2013.01)

(58) Field of Classification Search
CPC ... A61K 8/40; A61K 8/84; A61K 8/19; A61K 2800/30; A61Q 17/005; A01N 55/02
USPC ....................................... 424/618
See application file for complete search history.

(56) References Cited

U.S. PATENT DOCUMENTS

| 5,662,913 A * | 9/1997 | Capelli ................. A01N 59/16 424/405 |
|---|---|---|
| 2005/0186151 A1 | 8/2005 | Giroud |
| 2006/0057075 A1 | 3/2006 | Arkin et al. |
| 2006/0281663 A1 | 12/2006 | Asmus |
| 2006/0292086 A1 | 12/2006 | Curtis |
| 2009/0232860 A1 | 9/2009 | Larson et al. |
| 2009/0246258 A1 | 10/2009 | Shukla et al. |
| 2010/0196501 A1 | 8/2010 | Areskoug et al. |

FOREIGN PATENT DOCUMENTS

| CN | 102036773 A | 4/2011 |
|---|---|---|
| JP | 07188698 A | 7/1995 |
| JP | 3406970-D1 | 5/2003 |
| JP | 2012224571 A | 11/2012 |
| WO | WO9940791 A1 | 8/1999 |
| WO | WO0230204 A1 | 4/2002 |
| WO | WO2012018888 A2 | 2/2012 |
| WO | WO2012144476-D3 | 10/2012 |
| WO | WO2013026961-D2 | 2/2013 |

OTHER PUBLICATIONS

El Badawy et al: Inpact of environmental conditions (pH, ionic strength, and electrolyte type) on the surface charge and aggregation of silver nanoparticles suspensions. Environ Sci Technol. Jan. 25, 2010. vol. 44, No. 4, pp. 1260-1266.
Shen, Chemical Industry Press, Papermaking Chemicals, 2004, Edition 1, p. 279.
Tan et al: Synthesis of positively charged silver nanoparticles via photoreduction of $AgNO_3$ in branched polyethyleneimine/HEPES solution. Langmuir, Aug. 17, 2007. vol. 23, No. 19, pp. 9836-9843.
Yudovin-Faber et al: Quaternary Ammonium Polyethyleneimine: Antibacterial Activity. Journal of Nanomaterials, vol. 2010, pp. 1-11, published on or after May 8, 2010.
Lierop et al: Positively charged silver nanoparticles and their effect on Surface enhanced Raman scattering of dye-labelled oligonucleotides. The Royal Society of Chemistry 2012.

* cited by examiner

*Primary Examiner* — Yanzhi Zhang
(74) *Attorney, Agent, or Firm* — Laine IP OY

(57) ABSTRACT

Disinfection foam having low levels of alcohol, comprising at least water, foaming agent, and polymeric type silver ion source, and a method of manufacturing the same. The present antimicrobial foams are especially suitable for hand sanitizer foams, shaving foams, dry cleansing foams for full body, leave on shampoos, face cleansing foams and multipurpose dry cleaning.

7 Claims, No Drawings

METHOD OF PRODUCING A DISINFECTION FOAMABLE COMPOSITION

FIELD OF INVENTION

The invention relates to disinfection compositions. In particular, the present invention relates to novel multipurpose disinfection foams and foamable compositions. It also concerns methods of manufacturing such foams and compositions as well as to the uses thereof.

BACKGROUND ART

Alcohol hand sanitizers are widely accepted and used in the hospital and healthcare sectors. There are disadvantages in alcohol-based sanitizers. Thus, there is a lack of user comfortability and antimicrobial performance, especially long-term antimicrobial performance, is poor. There is no residual activity. Hands will be contaminated right after alcohol has evaporated, and the thickening agent used in the sanitizers will form a residual layer on the sanitized object, such as the user's hands, and offers a good substrate for microbial growth. Also alcohol itself can cause drying and irritation of skin. Alcohol is not effective against all known pathogens.

Patent publication WO 2012018888 describes an antiseptic liquid formulation, a method for its use, and a method for preparing the formulation. It contains a mixture of EDTA chelated silver ion and polyquaternium-69 polymer, which is said to bond chelated silver ions on the skin, and improve long term performance.

Silver based sanitizers suffer from stability problems, causing discoloration and performance issues. Also colloidal and particle based silver sanitizers can agglomerate and cause concentration differences.

Antimicrobial compositions are also described in JP 3406970, WO 2013/026961, WO 2012/144476 and US 2009/0246258.

None of the earlier publications discloses foams or foamable compositions which are stable and which exhibit an extended antimicrobial effect.

SUMMARY OF INVENTION

Technical Problem

There is a need for new and improved sanitizers which are low in alcohol content while simultaneously providing long-term effect.

There is also a need for methods of providing such compositions.

Solution to Problem

The present invention is based on the idea of formulating a multipurpose disinfection foam having low levels of alcohol, by mixing together water, foaming agent, and polymeric type silver ion source, optionally together with other components.

In a preferred embodiment, the present disinfection foams comprise a polymeric type silver ion source of the type formed by a silver salt of polyethyleneimine polymer.

It has been found that during formation of the polymer silver source, water molecules cause lack of stability to the final product. It is a feature of the present technology to produce polymeric silver source without any water.

More specifically, the present foams and foamable compositions are mainly characterized by what is stated in the characterizing part of claim 1.

Advantageous Effects of Invention

Considerable advantages are obtained by the present technical solution. Thus, a foaming low alcohol content hand sanitizer is provided which has excellent long lasting antimicrobial activity, enhanced stability and skin-feel properties over alcohol-based sanitizers. Foam sanitizer leaves smooth moisturized surface on skin without sticky residue, even after multiple applications. Silver ions eliminate effectively virus, bacteria, yeast and mold.

Enhanced stability of the composition is a considerable advantage. As will be discussed in more detail, during formation of the polymer silver source, by operating under in non-aqueous conditions, a stable product is obtained. Should the polymer, e.g. polyethylene imine, contain water, such water can also be removed before the addition of the silver salt to reach proper stability.

The foams and foamable compositions are suitable for sanitizing and cleansing or even disinfection of humans, animals and other living objects, as well as for treating, for example for the same purposes as mentioned above, inanimate objects, such as surfaces (e.g. door handles) which, when contaminated, become vehicles for communicable diseases.

Next, preferred embodiments will be examined more closely.

DETAILED DESCRIPTION OF EMBODIMENTS

As discussed above, the present disinfection foams or foamable compositions contain only small amounts of alcohol, and they basically comprise water, at least one foaming agent, and a polymeric type silver ion source. In particular, the polymeric type silver ion source is obtained by forming it without water. The latter feature includes the alternative of removing water from a water-containing polymer.

The polymer type silver ion source is a surprisingly beneficial antimicrobial additive for an antimicrobial foam or foamable composition according invention. Very low concentrations of silver ions are needed. Typically the concentration of the silver ions ranges from 10 to 2000 parts per million, especially from 20 to 200 parts per million of silver, calculated from the total weight of the composition.

Specific silver salts can be dispersed with polyethyleneimine to form stabile ionic dispersions, where silver ions are associated with amine groups of polyethyleneimine with ionic bonds.

Suitable silver salts to form polymeric silver ion source are preferably inorganic salts, such as silver chloride or silver sulfate, or organic salts, such as silver lactate. A polymeric silver ion source, of the present kind, is capable of forming molecular layers of silver polymer on skin.

Unexpectedly it was found that during polymer silver source formation any water molecules cause lack of stability to the final product. It is preferred to produce polymeric silver sources without any water. In case the polymer, e.g. polyethyleneimine, contains water, such water shall be removed before the addition of the silver salt. The problems relating to the presence of water has not been recognized earlier in the art.

Generally, the present compositions comprise at least the following components: water, foaming agent, and a polymeric type silver ion source. In addition, for use with humans, there can be agents which improve compatibility with skin contact and for adjusting pH. Examples include betaine for moisturizing effect and improved and skin feel, and lactic acid for adjustment of pH.

The alcohol content of the novel foams is low, typically less than 3.0% by weight of the total composition, in particular the total amount of lower alkanols (in particular ethanol) is less than 2.5%, preferably less than 1.0% by weight of the total composition. In one preferred embodiment, foams are produced which are free or essentially free (content less than 0.5% by weight) of alkanol.

In a first embodiment, the polymeric type silver ion source of the foam comprises a silver salt of polyethyleneimine polymer, in particular a silver salt of a polyethyleneimine polymer having a molecular weight of about 1,000 to 150,000 g/mol, for example about 20,000 to 120,000 g/mol, in particular about 35,000 to 100,000 g/mol.

In the foam or foamable composition according to the present invention, it is particularly preferred that the polymeric silver ion source is formed without water. Water can be removed if necessary, as discussed in the below example, before the polymeric components is contacted with a silver salt.

In particular, the water content of the polymeric component (before it is being contacted with the silver salt) is less than 5.0% by weight of the polymer, in particular less than 2%, preferably less than 1.0%, suitably less than 0.5%, for example less than 0.1 by weight of the polymer.

The non-aqueous polymer is then dispersed in a suitable medium, such as an alkanol, and contacted with a silver salt. The weight ratio of polymer to silver salt depends on the polymer and the silver salt used. Typically the weight ratio is about 5000:1 to 1:1, in particular 500:1 to 3:1, preferably about 250:1 to 4:1, for example about 50:1 to 5:1.

Contacting is preferably carried out under conditions conducive to achieving a reaction, in particular a chemical reaction, between the polymeric component and the silver component.

In one embodiment, the contacting step is continued until a clear solution of the polymeric component and the silver component is obtained. Typically, there is formed a soluble silver salt of the polymer and silver ions.

Although the composition is remarkably stable when prepared as explained herein, for further stabilizing the obtained solution, a stabilizing component can be added. Examples of such components are substances and compounds carrying sulfonamide functional group(s).

Thus, the stabilizer can for example be selected from the group comprising saccharin, cyclamic acid, sulfadiazine and acesulfame, saccharin being particularly preferred.

The stabilizers can also comprise organic acids, such as carboxylic acids, sulfonic acids and amino acids, phosphates, esters, aldehydes, ketones, zwitterionic compounds, titanates and their organic derivatives, silanes and their organic derivatives and organosulphur compounds.

The content of the stabilizer is typically 0.001 to 2.5 parts by weight, in particular 0.005 to 1 part by weight.

In the foamable composition, one or more foaming agents are further used. Such foaming agents can be selected from surface active compounds (i.e. surfactants). Typical foaming agents are sodium, magnesium and aluminium laureth sulfate and various amino oxide surfactants—in the compositions presented below lauramine oxide has been used. The content of the foaming agents is dependent on the chemical identity thereof; typically 0.01 to 10 parts by weight are added for 100 parts of water.

By mixing with water a composition formed by the polymeric silver salt, residues of alkanol, foaming agent(s), optionally together with stabilizer and adjuvants as explained above, a stable foam in obtained. Water makes up a majority of the foamable composition, typically 80 to 100% by weight of the total composition is water.

The term "stable" when used in present context, generally stands for foams which do not settle significantly and which do not exhibit significant discoloration and loss of antimicrobial efficiency.

The present compositions have long shelf life. In one embodiment, there is essentially no agglomeration or discernible discoloration of the foams over at least 30 minutes, preferably at least 2 hours, in particular at least 12 hours, advantageously at least 24 hours, suitably at least 96 hours from foaming. When kept in containers protected from natural light, there is essentially no agglomeration or discoloration of the foamable composition over at least 24 hours, in particular at least 7 days.

A foam produced as explained herein has a low level of alcohol, in particular the alcohol content, in terms of the total weight of ethanol and isopropyl alcohol, is less than 2.0 parts by weight, preferably less than 1.0 part by weight. Typically, the alcohol content is a residue of the alkanol used for the step of contacting the polymer with the silver salt. Thus, in one embodiment, the alkanol concentration is so small that the alkanol is of essentially no antimicrobial effect, at least not when compared with the silver component.

The pH of the foamable aqueous composition is typically in the range of 5.0 to 8.3, although these end points are not limiting. In one embodiment, the pH is preferably about 6.0 to 7.8, for example 6.5 to 7.5.

Based on the above, the present compositions can, in particular, contain the following components:

water 50 to 100 parts by weight, in particular 90 to 100 parts by weight;

a neutral chemical compound with a positively charged cationic functional group such as a quaternary ammonium or phosphonium, such as betaine, 0 to 5 parts by weight, in particular 0.1 to 3 parts by weight;

a foaming agent, such as lauramine oxide, 0.05 to 5 parts by weight, in particular 0.1 to 3 parts by weight;

a lower alcohol, such as isopropyl alcohol, 0 to 5 parts by weight, in particular 0.1 to 3 parts by weight;

a polymer, in particular polyethylene imine, e.g. PEI-1750, 0.01 to 10 parts by weight, in particular 0.05 to 5 parts by weight;

hydroxy acid, such as lactic acid, 0 to 10 parts by weight, in particular 0.01 to 2 parts by weight;

silver salt, such as silver chloride, 0.001 to 2.5 parts by weight, in particular 0.005 to 1 part by weight; and stabilizing compound(s), such as saccharin, 0.001 to 2.5 parts by weight, in particular 0.005 to 1 part by weight.

Antimicrobial foam of invention is especially suitable for hand sanitizer foams, shaving foams, dry cleansing foams for full body, leave on shampoos, face cleansing foams and multipurpose dry cleaning.

EXAMPLES

The inventive formulation achieves an unexpectedly large amount of quality, stable foam achieves enhanced and prolonged antimicrobial efficacy through the combination of silver ion activity and smooth distribution of silver ions.

The following non-limiting examples are provided for illustrative purposes only.

Example 1. Foam with a Silver Concentration of 90 ppm

A foamable antimicrobial composition of the invention was provided by first preparing silver polymer. Commercially available polyethyleneimine (PEI) grade (Epomin P-1050, Nippon Shokubai, molecular weight 70 000 g/mol) with high molecular weight was chosen for its low toxicity values. 51.14 g of Epomin P-1050 grade contains 25.57 g of water which was removed before the silver polymer was prepared. The water phase disturbs the reaction with the silver salt and can lead to unstable silver polymer, for which reason water was removed at elevated temperature of 100° C. under high vacuum. 25.57 g of PEI was then dissolved in 118.83 g of isopropyl alcohol to obtain easily mixable polymer solution. The solution was reacted together with 3.57 g of fine grain grade of silver chloride (Silver (I) chloride, Colonial Metals, MESH 325) by mixing at room temperature until a clear colorless solution was formed.

The obtained solution was further reacted with 2.03 g of acid saccharin (E-954, Productos Aditivos) to stabilize the silver polymer. Said solution was diluted with 295.83 litres of deionized water under vigorous mixing to obtain a solution with a silver content of 90 ppm. 120.0 g of lauramine oxide (Ammonyx LO, Stepan Company) was added to the solution to obtain foamable solution. For moisturizing effect and improved and skin feel 240.0 g of natural betaine (Betafin BP-20, DuPont) was added under stirring. Finally, the pH of the solution was adjusted to neutral 7 with an addition of 6.0 g of lactic acid. A clear stabile liquid was obtained having the following composition (the percentages are based on the weight of the total composition):

| | |
|---|---|
| Aqua | (98.28%) |
| Betaine | (0.80%) |
| Lauramine oxide | (0.40%) |
| Isopropyl alcohol | (0.39%) |
| PEI-1750 | (0.08%) |
| Lactic acid | (0.03%) |
| Silver chloride | (0.01%) |
| Saccharin | (0.01%) |

According to Hjelt Institute evaluation, the above formulation gives a log 6 result in EN1500 standard test by reducing microbial activity up to 99.9999%. The result is excellent compared to alcohol based sanitizers.

Example 2

Similarly, an antimicrobial foaming composition of the invention was prepared by first dissolving 2.29 g of polyethyleneimine (Epomin SP-018, Nippon Shokubai, molecular weight 1 800) with 7.09 g of isopropyl alcohol under vigorous mixing. Said solution was reacted with 0.34 g of silver chloride (Silver (I) chloride, Colonial Metals, MESH 325) and a clear colorless solution was formed. Obtained solution was further reacted with 0.18 g of acid saccharin (E-954, Productos Aditivos) to stabilize the silver polymer. Said solution was diluted with 2.96 litres of deionized water under vigorous mixing to obtain a solution with a silver content of 84 ppm. 4.50 g of PEG-12 dimethicone (SM3350P, KCC Silicones) and 12.00 g of decyl glucoside (Oramix NS10, Seppic) was added to the solution to obtain foamable solution. For moisturizing effect and improved and skin feel 15.00 g of natural betaine (Betafin BP-20, DuPont) was added under stirring.

According to Turku University of Applied Science ISO22196 test, the formula of Example 2 gave >log 5 microbial reduction.

INDUSTRIAL APPLICABILITY

The present invention can be used in hospital and healthcare sectors, but it can also be used in households and for sporting and outdoor (outing) applications. In this respect the composition can be characterized as being a multipurpose disinfection foam or foamable composition, which is suitable for two or more purposes selected from the group of disinfecting, sanitizing and cleansing of humans of animals and of inanimate objects.

The invention achieves manufacture of disinfection foam and foamable compositions which have properties of antimicrobial activity and which are suitable for hand sanitizers, shaving foams, dry cleansing foams for full body treatment, leave on shampoos, face cleansing and multipurpose dry cleaning.

LIST OF REFERENCES

Patent Literature

WO 2012/018888
JP 3406970
WO 2013/026961
WO 2012/144476
US 2009/0246258

The invention claimed is:

1. A method of producing a disinfection or foamable composition, the method comprising:
   removing a water content from a polyethyleneimene polymer such that the polyethyleneimene polymer comprises a water content of less than 2.0% by weight of the polymer,
   after the removing step, contacting a silver salt with the polyethyleneimine polymer to form a silver salt of the polyethyleneimine polymer, and
   mixing together water, a foaming agent, and the formed silver salt of the polyethyleneimine polymer to produce the disinfection or foamable composition, wherein the composition comprises an alcohol content of less than 3.0% by weight of the composition.

2. The method according to claim 1, wherein the alcohol content in the composition is less than 0.5% by weight of the composition.

3. The method according to claim 1, wherein a concentration of silver ions in the composition ranges from 20 to 200 parts per million, calculated from a total weight of the composition.

4. The method according to claim 1, wherein the silver salt of the polyethyleneimine polymer comprises a molecular weight of from about 1000 to 150,000 g/mol.

5. The method according to claim 1, further comprising dispersing the silver salt of the polyethylene-imine polymer within an alkanol at a weight ratio of from 50:1 to 5:1 for the contacting step with the silver salt.

6. The method according to claim 1, further comprising mixing an amount of saccharin with the water.

7. The method according to claim 1, further comprising mixing an amount of betaine for providing a moisturizer to the composition.

\* \* \* \* \*